United States Patent
Szymborski et al.

(10) Patent No.: US 11,682,284 B2
(45) Date of Patent: Jun. 20, 2023

(54) INTRUSION DETECTOR FOR A LORRY

(71) Applicant: CONTAINED TECHNOLOGIES UK LIMITED, London (GB)

(72) Inventors: Alex Szymborski, Prestbury (GB); Josh Lopez, Kurraba Point (AU); Henk Jan Oldenbandringh, Soest (NL)

(73) Assignee: Contained Technologies UK Limited, London (GB)

( * ) Notice: Subject to any disclaimer, the term of this patent is extended or adjusted under 35 U.S.C. 154(b) by 0 days.

(21) Appl. No.: 17/760,205

(22) PCT Filed: Feb. 8, 2021

(86) PCT No.: PCT/GB2021/050281
§ 371 (c)(1),
(2) Date: Aug. 5, 2022

(87) PCT Pub. No.: WO2021/156639
PCT Pub. Date: Aug. 12, 2021

(65) Prior Publication Data
US 2023/0066825 A1    Mar. 2, 2023

(51) Int. Cl.
*G08B 21/12* (2006.01)
*G01N 33/00* (2006.01)
(Continued)

(52) U.S. Cl.
CPC ............ *G08B 21/12* (2013.01); *B60R 25/102* (2013.01); *B60R 25/31* (2013.01); *B60R 25/32* (2013.01);
(Continued)

(58) Field of Classification Search
CPC ...... G08B 21/12; G08B 13/00; G08B 21/182; G08B 21/22; G08B 25/10; G08B 21/0269;
(Continued)

(56) References Cited

U.S. PATENT DOCUMENTS

| | | | |
|---|---|---|---|
| 10,169,975 B1 | 1/2019 | Payment | |
| 2006/0170537 A1* | 8/2006 | Marriott | B60R 25/1004 340/426.24 |

(Continued)

FOREIGN PATENT DOCUMENTS

| | | |
|---|---|---|
| CN | 204129884 | 7/2017 |
| GB | 2496374 | 5/2013 |

(Continued)

*Primary Examiner* — Ojiako K Nwugo
(74) *Attorney, Agent, or Firm* — Fleit Intellectual Property Law; Jose Gutman

(57) ABSTRACT

For various political, commercial and humanitarian reasons there is a desire to detect intrusion of stowaways into lorries and other freight vehicles. Many traditional intrusion detectors operate on the bases of detecting an increase in carbon dioxide within a space as indicator of presence of a human. A problem arises when the freight vehicle is carrying perishable goods such as fruits and vegetables which give off $CO_2$ as they perish which makes it difficult to reliably attribute the cause of an elevation in $CO_2$ concentration.

An embodiment of the invention overcomes this problem by detecting a sudden decrease in $CO_2$ concentration within the freight vehicle from a concentration that is much elevated from a background atmospheric concentration of around 400 ppm. This sudden decrease can be attributed to opening of a door of a trailer allowing the escape of $CO_2$ that has built up as the freight perishes.

12 Claims, 2 Drawing Sheets

(51) Int. Cl.
*G08B 13/00* (2006.01)
*G08B 25/10* (2006.01)
*B60R 25/102* (2013.01)
*B60R 25/31* (2013.01)
*B60R 25/32* (2013.01)
*B60R 25/33* (2013.01)
*G08B 21/18* (2006.01)
*G08B 21/22* (2006.01)

(52) U.S. Cl.
CPC ........... *B60R 25/33* (2013.01); *G01N 33/004* (2013.01); *G08B 13/00* (2013.01); *G08B 21/182* (2013.01); *G08B 21/22* (2013.01); *G08B 25/10* (2013.01)

(58) Field of Classification Search
CPC .... G01N 33/004; B60R 25/102; B60R 25/31; B60R 25/32; B60R 25/33
See application file for complete search history.

(56) References Cited

U.S. PATENT DOCUMENTS

| | | | |
|---|---|---|---|
| 2006/0181413 A1 | 8/2006 | Mostov | |
| 2008/0252450 A1* | 10/2008 | Wandel | B65D 55/026 340/541 |
| 2013/0015191 A1* | 1/2013 | Seagle | C08J 9/365 220/592.01 |
| 2013/0027556 A1 | 1/2013 | Clark et al. | |
| 2013/0033381 A1* | 2/2013 | Breed | G08B 13/2417 340/568.1 |
| 2014/0138276 A1* | 5/2014 | Smith | B65D 79/00 206/459.1 |

FOREIGN PATENT DOCUMENTS

| | | |
|---|---|---|
| GB | 2529000 | 10/2016 |
| WO | 2004005088 | 1/2004 |
| WO | 2019099497 | 5/2019 |

\* cited by examiner

INTRUSION DETECTOR FOR A LORRY

CROSS-REFERENCE TO RELATED APPLICATIONS

This application claims priority from and is related to the following prior application Patent Cooperation Treaty Patent PCT/GB2021/050281, filed on Feb. 8, 2021, which claims priority from Great Britain Patent Application No. 2001725.7, filed on Feb. 7, 2020. These prior applications, including the entirety of their written description and drawings, are collectively hereby incorporated by reference into the present application.

BACKGROUND

The present invention relates to intrusion detectors, and more particularly relates to an intrusion detector for a lorry based on detection of atmospheric carbon dioxide concentration.

For various political, commercial and humanitarian reasons there is a desire to detect intrusion of stowaways into lorries and other freight vehicles.

The background concentration of $CO_2$ within the atmosphere is currently around 400 parts per million (ppm). When a person enters a typical lorry trailer, the $CO_2$ concentration within the trailer rises to around 460 ppm within around 15 minutes as a result of the person's respiration. Each additional person present within the trailer increases the concentration by around 60 ppm.

Perishable goods such as fruits and vegetables give off $CO_2$ as they perish. In trials the inventors have determined that perishable goods within a lorry trailer can increase $CO_2$ concentration within the trailer from the background concentration to around 2000 ppm.

In initial trials, which were conducted using relatively small volumes of fruit and vegetables in non-air tight containers, this increase occurred over around a 15 minute period from closing the back of the trailer. In further trials with larger volumes of fruit and vegetables in reefer containers, which are substantially air tight, the rate of increase was significantly faster, reaching 2000 ppm level within a minute or two.

CA3036117 describes an alarm safety system that detects the presence of a person within a confined space by identifying an increase in carbon dioxide ($CO_2$) within the space. As perishable goods increase $CO_2$ concentration significantly more than people, the technique of CA3036117 does not allow for confident detection of intruders in trailers carrying perishable goods.

CN204129884 describes an anti-theft device intended to be placed by the window or door in a room and operate by detecting changes in $CO_2$ concentration. When the $CO_2$ concentration changes to be, without preference, higher or lower than a background $CO_2$ concentration range, an alarm is sounded.

U.S. Pat. No. 10,169,975 describes a method for detecting carbon dioxide in an enclosed space for the purpose of identifying whether an animal or child has been left unattended. It compares an actual decay rate of $CO_2$ concentration within the enclosed space with an expected decay rate. If the decay rate is faster or slower than the expected rate it enables an alert. A decay rate faster than expected is indicative that a door or window has been left open.

BRIEF SUMMARY

According to a first aspect of the invention there is provided a method of detecting intrusion of one or more persons into cargo hold of a vehicle carrying goods that emit carbon dioxide the method comprising identifying an intrusion event by detecting that a decrease in concentration of carbon dioxide within the cargo hold occurs at a time that a geographic location of the vehicle does not correspond with an expected loading or unloading location for the vehicle.

This helps to prevent the triggering of false alarms caused when the trailer is legitimately opened and closed to load and unload with cargo.

For example the intrusion event may be identified by detecting a decrease in concentration of carbon dioxide within the cargo hold of at least 400 ppm.

A decrease in $CO_2$ can be attributed to unauthorised access being made into the cargo hold as cargo holds typically remain closed during a journey.

Through experimentation, the inventors have identified that $CO_2$ concentration within a trailer holding $CO_2$ emitting goods reduces rapidly from an elevated concentration when a trailer door is opened. Therefore the intrusion event may be identified by detecting a relatively rapid decrease in concentration of carbon dioxide within the cargo hold towards the background atmospheric concentration as compared with the relatively slow increase in carbon dioxide concentration within the cargo hold that occurs as a result of emissions from the goods. An intrusion event may be identified by detecting a decrease in concentration of carbon dioxide within the cargo hold occurring at a rate of at least twenty percent within one second as rates of decrease equal or greater than this was commonly seen in the inventor's experimentation.

The goods may comprise perishable food items such as, for example, fruit and/or vegetables.

It is favourable that the method includes warning of a detected intrusion event and thus may comprise activating an alarm in response to detecting an intrusion event. Favourably the alarm is remote from the vehicle, e.g. at a monitoring station. This is because lorry drivers are often complicit in successful intrusion attempts and thus an alarm that was only for the driver's attention may be of limited benefit. When activated, the alarm may produce an alert, e.g. one or more of a visual, audible and haptic alert. The alert may comprise displaying a message on an electronic device, e.g. a computer screen, for viewing by a superintendent.

The method may comprise using manifest information to determine whether the cargo hold contains goods that emit $CO_2$; and if the cargo hold is determined to hold goods that emit $CO_2$, using the method in any of variations described above to detect an intrusion event; or if the cargo hold is determined not to be holding goods that emit $CO_2$, identifying an intrusion event by identifying an increase in $CO_2$ level within the cargo hold.

In this way intrusions can be detected irrespective of whether the trailer is carrying goods that emit $CO_2$ or not.

Identifying the intrusion event may comprise determining that the speed of the vehicle is above a threshold speed at substantially the time the decrease in concentration of carbon dioxide was detected.

In practice the vehicle needs to be stationary or travelling very slowly to allow for the trailer to be opened, stowaways to aboard and the trailer to be shut again. The threshold is set at a speed that makes this infeasible, for example twice human walking speed, between ~6-8 mph though a higher or lower value could be chosen. This aids to prevent false alarms.

Identifying the intrusion event may comprise using a light detector within the cargo hold to determine whether the detected decrease in concentration of carbon dioxide within the cargo hold coincides with an increase in ambient light level within the cargo hold. As many trailers let very little if any light to ingress into the hold, this helps affirm that a sharp drop in $CO_2$ is a consequence of opening of a door, rather than for some other reason or an error of the sensor.

The invention can also be described in terms of apparatus and thus according to another aspect of the invention there is provided apparatus according to claim 21.

The detection means may be arranged to identify the intrusion event by detecting a decrease in concentration of carbon dioxide within the cargo hold of at least 400 ppm.

The detection means may be arranged to identify the intrusion event by detecting a relatively rapid decrease in concentration of $CO_2$ within the cargo hold towards the background atmospheric concentration as compared with the relatively slow increase in $CO_2$ concentration within the cargo hold from a baseline concentration caused by emissions from the goods.

The detection means may be arranged to identify the intrusion event by detecting a decrease in concentration of $CO_2$ within the cargo hold occurring at a rate of at least twenty percent within one second.

The detection means may be arranged to output an event signal in response to identifying an intrusion event. The apparatus may comprise an alarm mechanism configured to produce an alarm signal in response to receiving the event signal.

The alarm mechanism is favourably located remotely from the vehicle.

The apparatus may comprise a store holding manifest information including an indication of whether there are $CO_2$ emitting goods in the cargo hold; and in which the detection means is configured to determine from the manifest whether there are $CO_2$ emitting goods in the cargo hold, and if the detection means determines that the cargo hold does not contain goods that emit carbon dioxide, identifying an intrusion event by identifying an increase in carbon dioxide level within the cargo hold.

The apparatus may comprise a speed determiner adapted to determine the speed of the vehicle, and the apparatus is adapted to determine an intrusion event by determining whether the speed of the vehicle is above a threshold speed at substantially the time the decrease in concentration of carbon dioxide was detected.

The apparatus may include a light detector within the cargo hold, and the apparatus may be adapted to use an output of the light sensor to determine whether the detected decrease in concentration of carbon dioxide within the cargo hold coincides with an increase in ambient light level within the cargo hold.

BRIEF DESCRIPTION OF THE DRAWINGS

The accompanying figures in which like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which.

DETAILED DESCRIPTION

As required, detailed embodiments are disclosed herein; however, it is to be understood that the disclosed embodiments are merely examples and that the devices and methods described herein can be embodied in various forms. Therefore, specific structural and functional details disclosed herein are not to be interpreted as limiting, but merely as a basis for the claims and as a representative basis for teaching one of ordinary skill in the art to variously employ the disclosed subject matter in virtually any appropriately detailed structure and function. Further, the terms and phrases used herein are not intended to be limiting, but rather, to provide an understandable description. Additionally, unless otherwise specifically expressed or clearly understood from the context of use, a term as used herein describes the singular and/or the plural of that term.

The terms "a" or "an", as used herein, are defined as one or more than one. The term "plurality", as used herein, is defined as two or more than two. The term "another", as used herein, is defined as at least a second or more. The terms "including" and "having," as used herein, are defined as comprising i.e., open language. The term "coupled," as used herein, is defined as "connected," although not necessarily directly, and not necessarily mechanically.

It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

Figure 1:
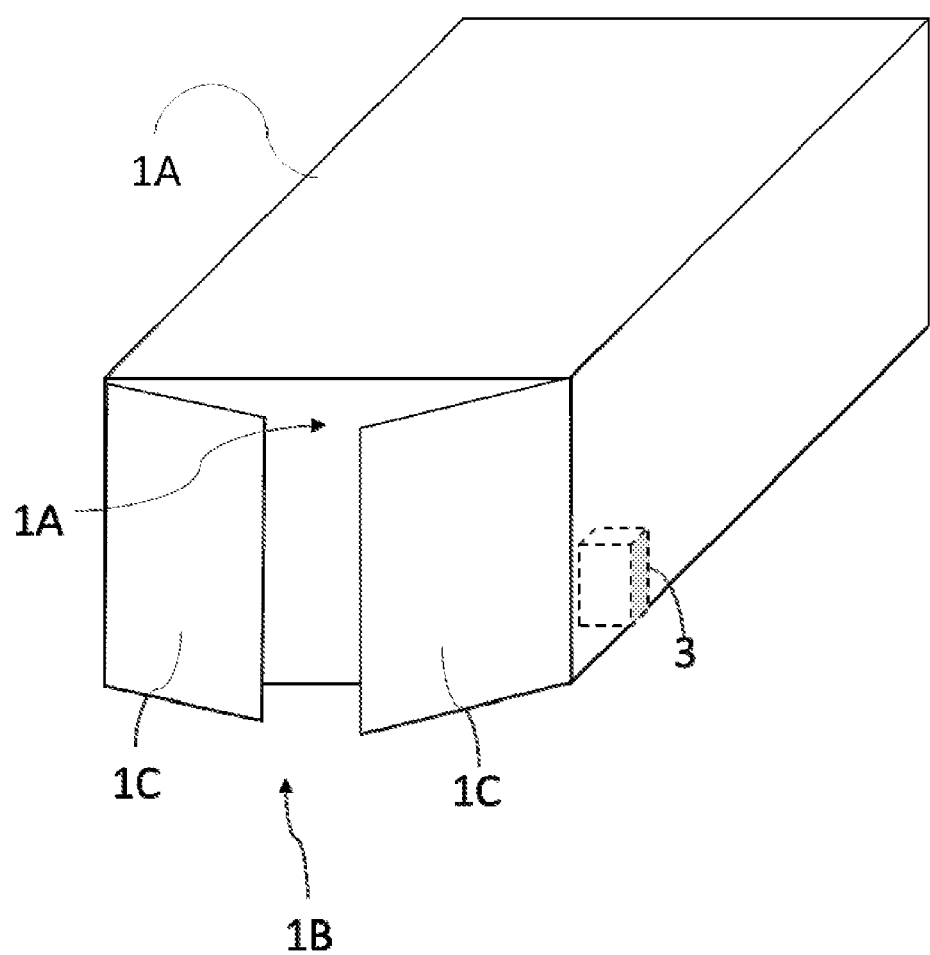
FIG. 1 is a schematic of a trailer for carrying goods having an intrusion sensing device.

FIG. 1 illustrates a trailer 1 that defines an interior space 1A for holding cargo and an intrusion sensor device 3 mounted to the trailer 1, e.g. within the interior space, for detecting intrusion of one or more persons into the trailer 1.

The trailer 1 includes an access 1B through which cargo can be loaded into and unloaded out from the trailer 1. The access 1B is closable by one or more doors 1C. The trailer 1 may, for example, take the form of a standardised shipping container such as used with intermodal freight transport that can be mounted on a lorry trailer chassis, or a custom design trailer built on a trailer chassis e.g. in the form of a box or a curtain sided trailer. The trailer 1 may be equipped with a refrigeration system (not shown) in order to control the internal temperature of the interior space 1A. The intrusion sensor device 3 may also be used to detect intrusion within vehicles in which the interior space 1A is defined by the chassis of the vehicle such as is the case in a van.

Figure 2:
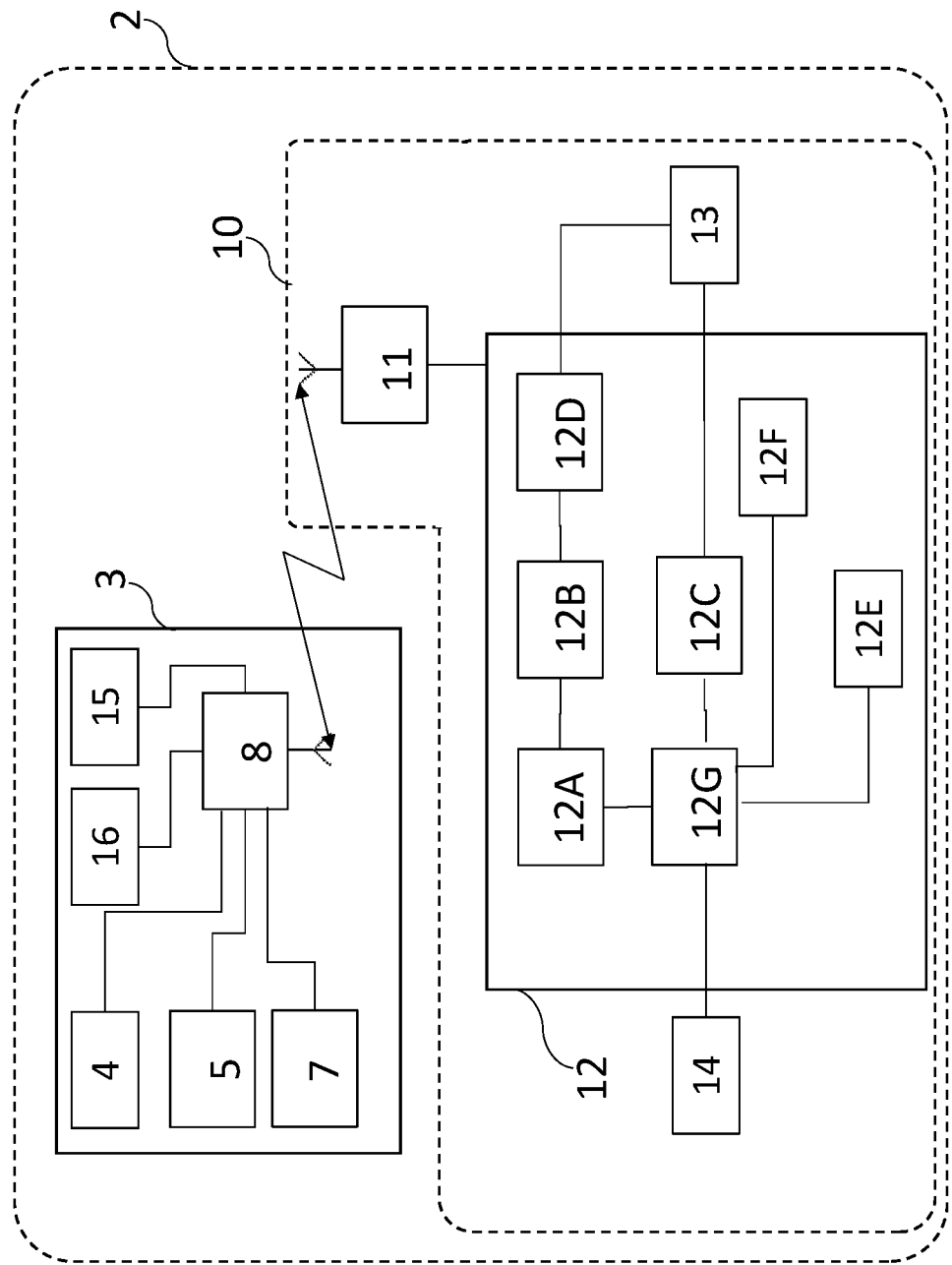
FIG. 2 is a schematic of an intrusion alarm system including the intrusion sensing device of FIG. 1.

With reference to FIG. 2, the intrusion sensor device 3 forms part of an intrusion alarm system 2 which also includes a monitoring system 10 located remotely from the intrusion sensor device 3 and trailer 1.

The intrusion alarm system 2 can be configured to detect intrusions in multiple trailers 1 simultaneously. Where so, each trailer 1 is equipped with its own separate intrusion sensor device 3.

The (or each where there are multiple of) intrusion sensor device 3 includes a carbon dioxide sensor 4, clock 5, global navigation satellite receiver (e.g. GPS receiver) 7, and a wireless transmitter 8. The carbon dioxide sensor 4 is configured to sense the concentration of carbon dioxide within the interior space 1A and output a signal indicative thereof, hereafter referred to as the $CO_2$ signal.

The wireless transmitter 8 is arranged to transmit the $CO_2$ signal, time data derived from the clock 5, and location information derived from the global navigation satellite receiver 7 to the remote monitoring system 10, e.g. via one or more of a cellular network, satellite network and the internet. The wireless transmitter 8 also transmits identification information (ID) of the intrusion sensor device 3 and/or trailer 1 stored by the intrusion sensor device 3 that is unique to the device-trailer combination.

The remote monitoring system 10 comprises a receiver 11, an intrusion detector 12, a store 13 that holds vehicle information, and an alarm 14.

The intrusion detector 12 includes the functions of a: $CO_2$ analyser 12A; configuration selector 12B; location comparator 12C; manifest lookup 12D; speed determiner 12E; motion analyser 12F and event signal generator 12G.

The functions of the intrusion detector 12 may be realised in a combination of hardware and software. An example combination of hardware and software could be a general purpose computer system (PC) with a computer program that, when being loaded and executed by the computer system, controls the computer system such that it carries out the functions described herein.

The vehicle information held in store 13, which may be in the form of a table, comprises an entry for each trailer 1 that carries an intrusion sensor device 3. Each entry includes the unique ID of the intrusion sensor device 3 or trailer 1; start and destination location information for one or more journeys of the trailer 1 and, for each journey, manifest information including an indicator of whether the trailer is carrying, for that journey, goods that emit $CO_2$. Where the vehicle information includes information for multiple journeys it may also hold time information relating to each journey, e.g. one or more of an expected start and finish time (or range of start and finish times) for each journey.

The receiver 11 is arranged to receive the $CO_2$ signal, time data, location information and ID information transmitted by the transmitter 8 and forward it to the intrusion detector 12.

The $CO_2$ analyser 12A of the intrusion detector 12 identifies a possible intrusion event from the received $CO_2$ signal and, depending on its configuration time data from clock 3, to identify an intrusion event from changes in carbon dioxide concentration within the interior space 1A.

In response to determining an intrusion event, the event signal generator 12G outputs an event signal to the alarm 14 which in response generates one or more of an audible, haptic and visual alert to warn a superintendent of the remote monitoring system of an intrusion.

The alert may comprise an electronic message (e.g. e-mail, instant message or SMS), for display on an electronic device (e.g. via electronic display), e.g. computer and/or phone. Where the alert comprises a message, the message may include information including the ID of the intrusion sensor device 3 and/or trailer 1 and location information of the trailer 1.

Upon receiving data from the intrusion sensor device 3, the intrusion detector 12 looks up the received ID in the vehicle journey information held in store 13 and the location comparator 12C compares the trailer's location as indicated by the location information with the start and destination location information of the relevant journey (if more than one is held) in order to determine whether the trailer 1 is at the start or destination of said journey. If it is determined that the trailer 1 is at either the start or destination location no event signal is generated in order to avoid false alarms as it is expected that the trailer's interior would be accessed legitimately at these locations.

This may be implemented by, for example, the location comparator 12C sending a signal to the event signal generator 12C that causes the event signal generator 12C to ignore any output from the $CO_2$ analyser 12A, or by sending a signal to prevent the $CO_2$ analyser from operating.

The $CO_2$ analyser 12A is configured by configuration selector 12B to operate in one of two ways depending on the nature of the goods held within the trailer 1. The manifest lookup 12D looks up manifest information from the vehicle journey information in store 13 to determine whether the trailer 1 is carrying $CO_2$ emitting goods and passes this to the configuration selector 12B. If the trailer 1 is carrying $CO_2$ emitting goods the configuration selector 12B configures the $CO_2$ analyser 12A to analyse the $CO_2$ signals and time signals in order to identify any decrease in $CO_2$ concentration within the interior space 1A occurring at a rate of at least twenty percent within a second. In response to identifying such an occurrence, the event signal generator 12G is caused to emit the event signal to the alarm 14.

If the manifest information indicates that the trailer 1 is not holding $CO_2$ emitting goods then the configuration selector 12B configures the analyser 12A to identify an increase in $CO_2$ concentration within the interior space 1A and in response to produce an event signal to the alarm 14. To reduce false positives, the intrusion detector 12 is configured to identify an increase in $CO_2$ concentration over atmospheric concentration above a threshold amount, e.g. 600 ppm.

An increase in $CO_2$ concentration within the trailer 1 is expected either because the interior space holds $CO_2$ emitting goods and/or humans that have stowed away within the trailer 1.

A rapid drop in $CO_2$ is expected as a result of $CO_2$ concentration within the trailer 1 having risen significantly above the atmospheric concentration, e.g. due to the presence of $CO_2$ emitting goods within the space 1A, before the interior space 1A being opened to the atmosphere through the opening of doors 1C which would allow $CO_2$ to escape quickly. For example, in a trailer carrying fresh fruit or vegetables, the $CO_2$ concentration within the trailer may be expected to rise to an elevated level of around 2000 ppm and would be expected to drop by at least 400 ppm equating to 20% of 2000 ppm, within a second as a result of the trailer door 1C opening.

To further reduce the instances of false positives, the speed determiner 12E is configured to use the location information and time information received from the intrusion device 3 to determine the speed of the trailer 1 and to prevent the generator 12G outputting an event signal if the trailer 1 is travelling above a threshold speed, e.g. 10 miles per hour, as stowaways are unlikely to be able to access the trailer 1 when it is travelling at speed.

The intrusion device 3 may include an impact and/or motion sensor (15) to detect an impact or motion of the intrusion device for the purpose of tamper detection. The output of the impact or motion sensor is transmitted by the transmitter 8 for receipt by the motion analyser 12F which determines from the output of the impact and/or motion sensor an attempt to tamper with the intrusion device by identifying impact or motion of the intrusion device that matches an impact or motion profile.

The intrusion device 3 may include a light sensor (16). The output of the light sensor may be used, together with the $CO_2$ signal by the intrusion detector 12 to detect an intrusion event, a sudden increase in brightness being indicative that a door 1C of the trailer 1 has been opened. The intrusion detector 12 may be configured such that the event signal generator 12G only generates an event signal in response to a detected increase in brightness at the time that the $CO_2$ within the cargo hold drops (or rises in the instance where only non-$CO_2$ emitting cargo is being transported).

The light sensor 16, speed determiner 12F, impact and/or motion sensor 15 and motion analyser 12F are all optional features.

In order to prolong battery life and/or provide resilience where the trailer is travelling through geographic regions with limited cellular network coverage, the intrusion sensor device may include a computer readable memory adapted to temporarily store multiple $CO_2$ concentration readings and to transmit said readings periodically or, where there is an interruption of connectivity with the intrusion detector 12, when connectivity with the intrusion detector 12 is re-established. For example, the intrusion sensor 3 may be arranged to take readings one or more times each second and to transmit said readings over the wireless connection to the intrusion detector once every few minutes.

Because many refrigerated trailers are designed such that the interior is substantially hermetically sealed from the exterior, in practice $CO_2$ concentrations would not be expected to drop markedly once elevated. Where so, an intrusion event can be accurately determined by detecting a marked drop in $CO_2$ concentration (e.g. at least 400 ppm) that occurs at some point within a timeframe in the order of minutes, e.g. 10-30 minutes, rather than seconds. In other words although the drop itself may have occurred within a second or two, it would only be necessary to determine that a drop occurred to a granularity of a 10-30 minute window. Where so this allows for significant power savings as the time interval between recording $CO_2$ concentrations and/or transmitting said readings can be increased significantly depending on the required accuracy of the data concerning the circumstances surrounding the intrusion event, e.g. time that event occurred, location of trailer at time of event.

In an alternative embodiment the function of the $CO_2$ analyser may be provided in the intrusion sensor device 3. In such an arrangement the carbon dioxide sensor 4 is configured to sense the concentration of carbon dioxide within the interior space 1A and output a signal indicative thereof directly to the $CO_2$ analyser. The $CO_2$ analyser uses the output from the sensor 4 together with the clock signal to identify an intrusion event as a result of determining either:
  i) decrease in $CO_2$ concentration within the interior space 1A of at least twenty percent occurring within a second; or
  ii) an increase in $CO_2$ concentration within the interior space 1A.

In response to determining a possible intrusion event, the $CO_2$ analyse outputs an event detection signal that is transmitted by the wireless transmitter 8 to the remote monitoring system 10.

The detection signal includes identification information (ID) of the intrusion sensor device 3 and/or trailer 1, location information of the trailer 1 derived from the global navigation satellite receiver 7, and an indicator of the cause that triggered the detection signal, i.e. either cause i) or ii) above. The remote monitoring system 10 uses the indicator of cause and the manifest information to determine whether to activate the alarm 14 upon receipt of an event detection signal. For example, if the detection signal was activated as a result of cause ii), the alarm 14 would not be activated if the manifest information indicated that the trailer held $CO_2$ producing goods.

The invention has application beyond lorry trailers to other freight vehicles, such as for example, goods wagons of freight trains.

Although the use of a global navigation satellite receiver is preferred obtaining position information of the vehicle could be obtained in other ways. For example, where transmitter 8 is adapted to communicate to a cellular wireless network, network cellular positioning could be used.

The Abstract is provided with the understanding that it is not intended be used to interpret or limit the scope or meaning of the claims. In addition, in the foregoing Detailed Description, various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The corresponding structures, materials, acts, and equivalents of all means or step plus function elements in the claims below are intended to include any structure, material, or act for performing the function in combination with other claimed elements as specifically claimed. The description herein has been presented for purposes of illustration and description, but is not intended to be exhaustive or limited to the examples in the form disclosed. Many modifications and variations will be apparent to those of ordinary skill in the art without departing from the scope of the examples presented or claimed. The disclosed embodiments were chosen and described in order to explain the principles of the embodiments and the practical application, and to enable others of ordinary skill in the art to understand the various embodiments with various modifications as are suited to the particular use contemplated. It is intended that the appended claims below cover any and all such applications, modifications, and variations within the scope of the embodiments.

Although specific embodiments of the subject matter have been disclosed, those having ordinary skill in the art will understand that changes can be made to the specific embodiments without departing from the scope of the disclosed subject matter. The scope of the disclosure is not to be restricted, therefore, to the specific embodiments, and it is intended that the appended claims cover any and all such applications, modifications, and embodiments within the scope of the present disclosure.

What is claimed is:

1. A method to detect intrusion of one or more persons into a cargo hold of a vehicle carrying goods that emit carbon dioxide, the method comprising:
   identifying an intrusion event by detecting that a decrease in concentration of carbon dioxide within the cargo hold occurs at a time that a geographic location of the vehicle does not correspond with an expected loading or unloading location for the vehicle.

2. The method according to claim 1, wherein the goods cause an increase in carbon dioxide concentration within the space from a baseline concentration, and in which the intrusion event is identified by detecting a relatively rapid decrease in concentration of carbon dioxide within the cargo hold towards the baseline concentration as compared with the rate of increase in carbon dioxide concentration caused by the goods.

3. The method according to claim 1, comprising activating an alarm in response to detecting an intrusion event.

4. The method according to claim 3, wherein the alarm is located remote from the vehicle.

5. The method according to claim 1, wherein the identifying the intrusion event comprises determining the speed of the vehicle is above a threshold speed at substantially the time the decrease in concentration of carbon dioxide was detected.

6. The method according to claim 1, wherein the identifying the intrusion event comprises using a light detector within the cargo hold to determine whether the detected decrease in concentration of carbon dioxide within the cargo hold coincides with an increase in ambient light level within the cargo hold.

7. A method of detecting intrusion of one or more persons in a cargo hold of a vehicle, the method comprising:
   determining from a manifest whether the cargo hold is holding goods that emit carbon dioxide;
   if the cargo hold is determined to hold goods that emit carbon dioxide, identifying an intrusion event by detecting that a decrease in concentration of carbon dioxide within the cargo hold occurs at a time that a geographic location of the vehicle does not correspond with an expected loading or unloading location for the vehicle; and
   if the cargo hold is determined not to be holding goods that emit carbon dioxide, warning of an intrusion event by identifying an increase in carbon dioxide level within the cargo hold.

8. An apparatus for detecting intrusion of one or more persons in a cargo hold of a vehicle carrying goods that emit carbon dioxide; the apparatus comprising:
   a sensor to sense the concentration of carbon dioxide within the cargo hold and output a signal indicative thereof;
   a positioning system providing geographical location information of the vehicle; and
   a detector arranged to receive the signal from the sensor and use the geographic location information to identify an intrusion event by detecting that a decrease in concentration of carbon dioxide within the cargo hold occurs at a time that that the vehicle's location does not correspond with an expected loading or unloading location for the vehicle.

9. The apparatus according to claim 8, comprising:
   a store holding manifest information including an indication of whether there are $CO_2$ emitting goods in the cargo hold; and
   in which the detector is configured to determine from the manifest whether there are $CO_2$ emitting goods in the cargo hold, and if the detector determines that the cargo hold does not contain goods that emit carbon dioxide, identifying an intrusion event by identifying an increase in carbon dioxide level within the cargo hold.

10. The apparatus according to claim 8, wherein the goods cause an increase in carbon dioxide concentration within the cargo hold from a baseline concentration, and in which the detector is arranged to identify the intrusion event by detecting a relatively rapid decrease in concentration of carbon dioxide within the cargo hold towards the baseline concentration as compared with the rate of increase in carbon dioxide concentration caused by the goods.

11. The apparatus according to claim 10, wherein the detector is arranged to output an event signal in response to identifying an intrusion event and the system comprising an alarm mechanism configured to activate to produce an alarm signal in response to receiving the event signal.

12. The apparatus according to claim 11, wherein the alarm mechanism is located remote from the vehicle.

\* \* \* \* \*